US006368359B1

(12) United States Patent
Perry et al.

(10) Patent No.: US 6,368,359 B1
(45) Date of Patent: Apr. 9, 2002

(54) PROCESS FOR STABILIZATION OF DRY CLEANING SOLUTIONS

(75) Inventors: Robert J. Perry, Niskayuna; Donna A. Riccio, Watervliet, both of NY (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/466,484

(22) Filed: Dec. 17, 1999

(51) Int. Cl.⁷ .............................. D06L 1/08; D06L 1/10; C07F 7/20
(52) U.S. Cl. .............................. 8/142; 134/13; 556/456
(58) Field of Search .............................. 8/142; 134/13; 510/285, 291; 556/456

(56) References Cited

U.S. PATENT DOCUMENTS

| 4,661,612 A | | 4/1987 | George et al. |
| 4,774,346 A | | 9/1988 | Imai et al. |
| 5,118,764 A | | 6/1992 | Ichinohe et al. |
| 5,225,509 A | | 7/1993 | Heinrich et al. |
| 5,238,899 A | | 8/1993 | Kadowaki et al. |
| 5,245,067 A | | 9/1993 | Schneider et al. |
| 5,312,947 A | * | 5/1994 | Tsukuno et al. |
| 5,782,983 A | * | 7/1998 | Inada et al. |
| 6,068,635 A | * | 7/2000 | Berndt et al. |

FOREIGN PATENT DOCUMENTS

EP   543 665   5/1993

* cited by examiner

*Primary Examiner*—Margaret Einsmann

(57) ABSTRACT

A method for stabilizing silicone dry cleaning solvents that may contain an undesirable basic impurity capable of causing cyclic siloxane formation, comprising contacting the silicone solvent with an aqueous solution, and separating the silicone solvent.

18 Claims, No Drawings

PROCESS FOR STABILIZATION OF DRY CLEANING SOLUTIONS

TECHNICAL FIELD

The present invention is directed to a process, more specifically, to a process for stabilizing silicone dry cleaning solvents containing basic impurities.

BACKGROUND

Current dry cleaning technology uses perchloroethylene ("PERC") or petroleum-based materials as the cleaning solvent. PERC suffers from toxicity and odor issues. The petroleum-based products are not as effective as PERC in cleaning garments. Volatile siloxanes are being introduced into the dry cleaning industry as an alternative to PERC. However, there exists a need to stabilize the siloxane solvents to prevent undesirable cyclic siloxane ($D_4$) formation and polymerization.

Methods for the purification of organopolysiloxanes have previously been reported, but they have not been reported for the purification of certain cyclic siloxanes ($D_5$). Methods for purifying organopolysiloxanes utilizing elemental metals has been reported (see U.S. Pat. No. 5,245,067). Other patents disclose the purification of polyether silicones by contacting with an aqueous acid and removing the odorous materials formed (see U.S. Pat. No. 5,118,764), or the reaction with hydrogen and a hydrogenation catalyst (see U.S. Pat. No. 5,225,509). Hexamethyldisiloxane has been purified by successive treatments with a condensation catalyst, washing with water, separating the phases, distilling the siloxane, treating with acid clay and then treating with activated carbon (see U.S. Pat. No. 4,774,346). Siloxanes have also been purified by contacting with steam and distilling out the impurities (see EP 543 665). A deodorization method utilizing active carbon to which a functional group has been fixed through a silanol bond has been reported (see U.S. Pat. No. 5,238,899). Finally, a method was reported for purifying silicone oil by adding a drying agent and an adsorption agent to silicone and passing a low water vapor inert gas through the system (see U.S. Pat. No. 4,661,612).

What is needed in the art is an aqueous extraction system that renders the base catalyst inactive, stabilizes the siloxane and suppresses reequilibration and polymerization.

SUMMARY OF THE INVENTION

In a first aspect, the present invention is directed to a method for stabilizing silicone dry cleaning solvents that may contain an undesirable basic impurity capable of causing cyclic siloxane formation, comprising contacting the silicone solvent with an aqueous solution to purify the solvent and then separating the silicone solvent.

The process of the present invention is effective in preventing formation of certain cyclic siloxanes (i.e., $D_4$) that are undesirable in the silicone solvent.

As used herein, the terms $D_4$, $D_5$ and $D_6$ refer to cyclic siloxanes having the formula: —$(R_2SiO)_x$— where x is 4, 5 or 6 (i.e., $D_5$ is decamethylcyclopentasiloxane).

DETAILED DESCRIPTION OF THE INVENTION

Preferably, the first preferred embodiment of the method of the present invention comprises, contacting a silicone dry cleaning solvent that may contain an undesirable basic impurity capable of causing cyclic siloxane formation with an aqueous solution, agitating to ensure good mixing of the solvent and the aqueous solution, and separating the silicone solvent. The aqueous solution can be a salt solution or a series of dilute aqueous acid and base solutions.

Base catalysts that promote reequilibration and redistribution include, but are not limited to, potassium silanolate, potassium hydroxide, tetramethylammonium hydroxide, tetrabutylphosphonium hydroxide and the like.

Solutions suitable as extractants are aqueous solutions of the formula:

MeX wherein Me refers to alkali metals and alkaline earth metals, such as sodium, magnesium, potassium, calcium and the like, and X refers to halogens, such as chlorine, bromine, fluorine and the like, or chalcogen derivatives, such as sulfates, carbonates, bicarbonates, acetates and the like. Examples of suitable solutions include but are not limited to sodium chloride, potassium chloride, sodium bromide, magnesium sulfate and the like.

Also suitable are dilute aqueous acid mixtures and base mixtures such as acetic acid, citric acid, sorbic acid, sodium carbonate and sodium bicarbonate.

After extraction, the silicone solvent may be dried with a suitable drying agent such as 4A molecular sieves, 13X molecular sieves, magnesium sulfate, calcium chloride and calcium sulfate.

Preferably, the silicone dry cleaning solvent is a volatile linear, branched, cyclic or a combination thereof, siloxane.

Compounds suitable as the linear or branched, volatile siloxane solvent of the present invention are those containing a polysiloxane structure that includes from 2 to 20 silicon atoms. Preferably, the linear or branched, volatile siloxanes are relatively volatile materials, having, for example, a boiling of below about 300° C. point at a pressure of 760 millimeters of mercury ("mm Hg").

In a preferred embodiment, the linear or branched, volatile siloxane comprises one or more compounds of the structural formula (I):

$$M_{2+y+2z}D_xT_yQ_z \qquad (I)$$

wherein:

M is $R^1{}_3SiO_{1/2}$;

D is $R^2{}_2SiO_{2/2}$;

T is $R^3SiO_{3/2}$;

and Q is $SiO_{4/2}$ $R^1$, $R^2$ and $R^3$ are each independently a monovalent hydrocarbon radical; and x and y are each integers, wherein $0 \leq x \leq 10$ and $0 \leq y \leq 10$ and $0 \leq z \leq 10$.

Suitable monovalent hydrocarbon groups include acyclic hydrocarbon radicals, monovalent alicyclic hydrocarbon radicals, monovalent and aromatic hydrocarbon radicals. Preferred monovalent hydrocarbon radicals are monovalent alkyl radicals, monovalent aryl radicals and monovalent aralkyl radicals.

As used herein, the term "($C_1$–$C_6$)alkyl" means a linear or branched alkyl group containing from 1 to 6 carbons per group, such as, for example, methyl, ethyl, propyl, isopropyl, n-butyl, iso-butyl, sec-butyl, tert-butyl, pentyl, hexyl, preferably methyl.

As used herein, the term "aryl" means a monovalent unsaturated hydrocarbon ring system containing one or more aromatic rings per group, which may optionally be substituted on the one or more aromatic rings, preferably with one or more ($C_1$–$C_6$)alkyl groups and which, in the case of two or more rings, may be fused rings, including, for example, phenyl, 2,4,6-trimethylphenyl, 2-isopropylmethylphenyl, 1-pentalenyl, naphthyl, anthryl, preferably phenyl.

As used herein, the term "aralkyl" means an aryl derivative of an alkyl group, preferably a ($C_2$–$C_6$)alkyl group, wherein the alkyl portion of the aryl derivative may, optionally, be interrupted by an oxygen atom, such as, for example, phenylethyl, phenylpropyl, 2-(1-naphthyl)ethyl, preferably phenylpropyl, phenyoxypropyl, biphenyloxypropyl.

In a preferred embodiment, the monovalent hydrocarbon radical is a monovalent ($C_1$–$C_6$)alkyl radical, most preferably, methyl.

In a preferred embodiment, the linear or branched, volatile siloxane comprises one or more of, hexamethyldisiloxane, octamethyltrisiloxane, decamethyltetrasiloxane, dodecamethylpentasiloxane, tetradecamethylhexasiloxane or hexadecamethylheptasiloxane or methyltris(trimethylsiloxy)silane. In a more highly preferred embodiment, the linear or branched, volatile siloxane of the present invention comprises octamethyltrisiloxane, decamethyltetrasiloxane, or dodecamethylpentasiloxane or methyltris(trimethylsiloxy)silane. In a highly preferred embodiment, the siloxane component of the composition of the present invention consists essentially of decamethyltetrasiloxane.

Suitable linear or branched volatile siloxanes are made by known methods, such as, for example, hydrolysis and condensation of one or more of tetrachlorosilane, methyltrichlorosilane, dimethyldichlorosilane, trimethylchlorosilane, or by isolation of the desired fraction of an equilibrate mixture of hexamethyldisiloxane and octamethylcyclotetrasiloxane or the like and are commercially available.

Compounds suitable as the cyclic siloxane component of the present invention are those containing a polysiloxane ring structure that includes from 2 to 20 silicon atoms in the ring. Preferably, the linear, volatile siloxanes and cyclic siloxanes are relatively volatile materials, having, for example, a boiling point of below about 300° C. at a pressure of 760 millimeters of mercury ("mm Hg").

In a preferred embodiment, the cyclic siloxane component comprises one or more compounds of the structural formula (II):

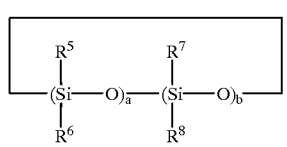

(II)

wherein:

$R^5$, $R^6$, $R^7$ and $R^8$ are each independently a monovalent hydrocarbon group; and a and b are each integers wherein $0 \leq a \leq 10$ and $0 \leq b \leq 10$, provided that $3 \leq (a+b) \leq 10$.

In a preferred embodiment, the cyclic siloxane comprises one or more of, octamethylcyclotetrasiloxane, decamethylcyclopentasiloxane, dodecamethylcyclohexasiloxane, tetradecamethylcycloheptasiloxane. In a more highly preferred embodiment, the cyclic siloxane of the present invention comprises octamethylcyclotetrasiloxane or decamethylcyclopentasiloxane. In a highly preferred embodiment, the cyclic siloxane component of the composition of the present invention consists essentially of decamethylcyclopentasiloxane.

Suitable cyclic siloxanes are made by known methods, such as, for example, hydrolysis and condensation of dimethyldichlorosilane and are commercially available.

It is believed that those dry cleaning solvents useful in the present invention that lack a cyclic siloxane component would be more stable than those which include a cyclic siloxane component, in that cyclic siloxanes are known to ring open and polymerize under acidic and basic conditions.

In a first embodiment of the method of the present invention, approximately 100 parts by weight ("pbw") of siloxane solvent is contacted with up to 1000, more preferably up to 500, even more preferably up to 100 pbw of an aqueous salt or weak acid mixture which could be followed by a weak base mixture treatment or a combination thereof for 0.001 to 6 hours at 10 to 80° C. After the siloxane solvent has contacted the aqueous solution for the appropriate time and has been purified, the siloxane solvent is separated from the mixture and dried if necessary, and then the solvent can be recycled in the dry cleaning apparatus. The method of the present invention effectively reduces the level of impurities in the silicone solvent.

In a second embodiment of the method of the present invention, a dry cleaning fluid is treated by the method of the present invention.

The method of the present invention also comprises a dry cleaning process comprising the steps of: contacting an article with a silicone solvent, and removing the silicone solvent, then treating the silicone solvent that has been removed with an aqueous solution, agitating to ensure good mixing of the solvent and the aqueous solution, and separating the silicone solvent, then reusing the treated silicone solvent in the dry cleaning process.

The following examples illustrate the process of the present invention. They are illustrative and the claims are not to be construed as limited to the examples.

EXAMPLE 1

Decamethylcyclopentasiloxane ($D_5$) was mixed with a base catalyst (potassium silanolate with a potassium hydroxide equivalence of approximately 4%) to make a stock solution containing 200 parts per million ("ppm") potassium hydroxide. Aliquots of the stock solution were shaken with various concentrations of NaCl solutions and then separated or separated and dried at ambient temperature. The silicone solvent was then heated to 100° C. and cyclic levels were monitored over time as shown in table.

TABLE 1

Treatment of Contaminated $D_5$ by Contacting with Aqueous Salt Solutions (200 ppm KOH equiv.)

| Exp | NaCl soln | Dried (Y/N) | Time (h) | % $D_4$ | % $D_5$ | % $D_6$ | Time (h) | % $D_4$ | % $D_5$ | % $D_6$ |
|---|---|---|---|---|---|---|---|---|---|---|
| 1 | None | Control | 2 | 1.17 | 96.05 | 1.59 | 23 | 6.84 | 89.81 | 3.35 |
| 2 | 0.05 M | N | 2 | 0 | 99.6% | .4% | 23 | 0 | 99.56 | .44% |
| 3 | 0.05 M | Y | 2 | 0 | 99.6% | .4% | 23 | 0 | 99.48 | .52% |
| 4 | 0.5 M | N | 2 | 0 | 99.46 | .54% | 23 | 0 | 99.47 | .53% |
| 5 | 0.5 M | Y | 2 | 0 | 99.6% | .4% | 23 | 0 | 99.57 | .43% |
| 6 | 5.0 M | N | 2 | 0 | 99.48 | .52% | 23 | 0 | 99.48 | .52% |
| 7 | 5.0 M | Y | 2 | 0 | 99.56 | .44% | 23 | 0 | 99.57 | .43% |
| 8 | water | N | 2 | 0 | 99.57 | .43% | 23 | 0 | 99.56 | .44% |
| 9 | water | Y | 2 | 0 | 99.6 | .40% | 23 | 0 | 99.57 | .43% |

The base catalyst readily initiated polymerization and reequilibration of the $D_5$ as shown by experiment 1. Contacting the contaminated silicone solvent with water or salt solutions and then separating the solvent gave a stable silicone mixture that did not polymerize or reequilibrate. The salt solutions served to more efficiently allow separation of the aqueous and silicone phases.

EXAMPLE 2

The same stock solution from Example 1 was treated with a dilute solution of acid followed by separation of the siloxane layer and then treatment with dilute base and then separation and drying as shown in table 2. The silicone solvent was heated to 100° C. for 2 hours and cyclic levels were measured. Heat was continued until 18 hours, and cyclic levels were again measured.

TABLE 2

Treatment of Contaminated $D_5$ by Contacting with Aqueous Acid and Base Solutions (200 ppm KOH equiv.)

| Exp | Acid | Base | Dried (Y/N) | Time (h) | % $D_5$ | % $D_6$ | Time (h) | % $D_5$ | % $D_6$ |
|---|---|---|---|---|---|---|---|---|---|
| 10 | 0.01 AcOH | 0.01 NaHCO$_3$ | N | 2 | 99.57 | .43% | 23 | 99.57 | .43% |
| 11 | 0.01 AcOH | 0.01 NaHCO$_3$ | Y | 2 | 99.58 | .42% | 23 | 99.58 | .42% |
| 12 | 0.01 AcOH | — | N | 2 | 99.58 | .41% | 23 | 99.54 | 0.46% |
| 13 | 0.01 AcOH | — | Y | 2 | 99.9 | .10% | 23 | 99.9 | 0.10% |
| 14 | Citric | 0.01 NaHCO$_3$ | N | 2 | 99.6 | .40% | 23 | 99.9 | 0.10% |
| 15 | Citric | 0.01 NaHCO$_3$ | Y | 2 | 99.61 | .39% | 23 | 99.56 | 0.44% |
| 16 | Citric | — | N | 2 | 99.6 | .40% | 23 | 99.9 | 0.10% |
| 17 | Citric | — | Y | 2 | 99.9 | .10% | 23 | 99.6 | 0.40% |
| 18 | Sorbic | 0.01 NaHCO$_3$ | N | 2 | 99.6 | .40% | 23 | 99.6 | 0.40% |
| 19 | Sorbic | 0.01 NaHCO$_3$ | Y | 2 | 99.55 | .44% | 23 | 99.54 | 0.46% |
| 20 | Sorbic | — | N | 2 | 99.6 | .40% | 23 | 99.60 | 0.40 |
| 21 | Sorbic | — | Y | 2 | 99.6 | .40% | 23 | 99.6 | 0.40% |

*$D_4$ level was 0 at 2 hours and 23 hours showing no $D_4$ formation.

Treatment with dilute solutions of weak acids and bases effectively prevented undesired reequilibration and polymerization.

EXAMPLE 3

The same experiment as Example 1 was conducted using a linear siloxane solvent ($MD_2M$). Results of the experiment are shown in Table 3.

TABLE 3

Treatment of Contaminated $MD_2M$ by Contacting with Aqueous Salt Solutions (200 ppm KOH equiv.)

| Exp | NaCl soln | Dried (Y/N) | Time (h) | % MDM | % $MD_2M$ | % $MD_3M$ | Time (h) | % MDM | % $MD_2M$ | % $MD_3M$ |
|---|---|---|---|---|---|---|---|---|---|---|
| 22 | None | Control | 2 | 9.1 | 69.8 | 10.4 | 24 | 28.39 | 25.33 | 16.16 |
| 23 | 0.05 M | N | 2 | 0 | 99.9 | .10 | 24 | 0 | 99.91 | .09 |
| 24 | 0.05 M | Y | 2 | 0 | 99.53 | .47 | 24 | 0 | 99.82 | .18 |
| 25 | 0.5 M | N | 2 | 0 | 99.16 | .84 | 24 | 0 | 99.44 | .55 |
| 26 | 0.5 M | Y | 2 | 0 | 99.72 | .28 | 24 | 0 | 99.28 | .72 |
| 27 | 5.0 M | N | 2 | 0 | 99.99 | .10 | 24 | 0 | 99.96 | .04 |
| 28 | 5.0 M | Y | 2 | 0 | 99.78 | .22 | 24 | 0 | 99.95 | .05 |
| 29 | Water | N | 2 | 0 | 99.9 | .10 | 24 | 0 | 99.74 | .25 |
| 30 | Water | Y | 2 | 0 | 99.9 | .10 | 24 | 0 | 99.87 | .12 |

Table 3 shows that contacting linear siloxane dry cleaning solvents with water and salt solutions is also effective at stabilizing the dry cleaning solvent with respect to base catalysis.

EXAMPLE 4

Another experiment was conducted in the same manner as Example 2 using a linear silicone solvent ($MD_2M$). The results are shown below in Table 4.

TABLE 4

Treatment of Contaminated $MD_2M$ by Contacting with Aqueous Acid and Base Solutions. (200 ppm KOH equiv.)

| Exp | Acid | Base | Dried (Y/N) | Time (h) | % $MD_2M$ | % $MD_3M$ | Time (h) | % $MD_2M$ | % $MD_3M$ |
|---|---|---|---|---|---|---|---|---|---|
| 31 | 0.01 AcOH | 0.01 $NaHCO_3$ | N | 2 | 99.79 | .21 | 24 | 99.94 | .06 |
| 32 | 0.01 AcOH | 0.01 $NaHCO_3$ | Y | 2 | 99.92 | .05 | 24 | 99.84 | .16 |
| 33 | Citric | - | N | 2 | 99.90 | .10 | 24 | 99.91 | .81 |
| 34 | Citric | - | Y | 2 | 99.89 | .11 | 24 | 99.42 | .58 |
| 35 | Sorbic | - | N | 2 | 99.92 | .08 | 24 | 99.74 | .26 |
| 36 | Sorbic | - | Y | 2 | 99.89 | .11 | 24 | 99.91 | .09 |

*% MDM levels were 0 at 2 hours and 24 hours, showing no MDM formation.

Table 4 illustrates that treatment with dilute solutions of weak acids and bases effectively prevented undesired reequilibration and polymerization.

EXAMPLE 5

Cyclic silicone solvent ($D_5$) containing varying concentrations of base were treated with salt solutions. The results are shown in Table 5.

TABLE 5

Treatment of Contaminated $D_5$ by 0.5 M Salt Solutions with varying amounts of base

| Exp | KOH ppm | Dried (Y/N) | Time (h) | % $D_4$ | % $D_5$ | % $D_6$ | Time (h) | % $D_4$ | % $D_5$ | % $D_6$ |
|---|---|---|---|---|---|---|---|---|---|---|
| 37 | 200 | N | 2 | 0 | 99.45 | .55 | 24 | 0 | 99.45 | .55 |
| 38 | 200 | Y | 2 | 0 | 99.45 | .55 | 24 | 0 | 99.46 | .54 |
| 39 | 500 | N | 2 | 0 | 99.55 | .45 | 24 | 0 | 99.46 | .54 |
| 40 | 500 | Y | 2 | 0 | 99.32 | .68 | 24 | 0 | 99.47 | .53 |
| 41 | 1000 | N | 2 | 0 | 99.49 | .51 | 24 | 0 | 99.48 | .50 |
| 42 | 1000 | Y | 2 | 0 | 99.48 | .52 | 24 | 0 | 99.50 | .50 |

Table 5 illustrates that up to 1000 ppm base in a silicone solvent can be rendered unreactive when contacted with aqueous salt solutions.

EXAMPLE 6

Cyclic silicone solvent ($D_5$) containing varying concentrations of base were treated with varying amounts of water. The results are shown in Table 6.

TABLE 6

Treatment of Contaminated $D_5$ with varying amounts of water.

| Exp | $D_5:H_2O$ ratio | Dried (Y/N) | Time (h) | % $D_4$ | % $D_5$ | % $D_6$ | Time (h) | % $D_4$ | % $D_5$ | % $D_6$ |
|---|---|---|---|---|---|---|---|---|---|---|
| 43 | 100:1 | N | 2 | N/A | N/A | N/A | 22 | 0 | 99.46 | .54 |
| 44 | 10:1 | N | 2 | 0 | 99.57 | .43 | 23 | 0 | 99.56 | .44 |
| 45 | 1:1 | N | 2 | N/A | N/A | N/A | 22 | 0 | 99.47 | .53 |

Table 6 illustrates that contacting base containing silicone solvents with aqueous systems at various ratios of silicone solvent to water are effective in suppressing polymerization and reequilibration.

What is claimed is:

1. A method for stabilizing silicone dry cleaning solvents that contain an undesirable basic impurity capable of causing cyclic siloxane formation comprising, contacting a silicone dry cleaning solvent with an aqueous solution comprising a salt or a weak acid at a temperature of from about 10° C. to about 80° C., and separating the silicone solvent wherein said dry cleaning solvent is purified of said undesirable basic impurity.

2. The method of claim 1, further comprising agitating to ensure good mixing of the solvent and the aqueous solution.

3. The method of claim 1, wherein the aqueous solution used is up to 1000 parts by weight per 100 parts by weight of silicone solvent.

4. The method of claim 1, wherein the aqueous solution used is a solution of sodium chloride, potassium chloride, sodium bromide, magnesium sulfate, acetic acid, citric acid, sorbic acid, sodium carbonate and sodium bicarbonate.

5. The method of claim 1, further comprising drying the solvent with an adsorbent.

6. The method of claim 5, wherein the adsorbent used is selected from the group consisting of 4A molecular sieves, 13X molecular sieves, magnesium sulfate, calcium chloride and calcium sulfate.

7. The method of claim 1, wherein the solvent is a linear or branched siloxane comprising one or more compounds of the structural formula:

$$M_{2+y+2z}D_xT_yQ_z$$

wherein:

M is $R^1_3SiO_{1/2}$;

D is $R^2_2SiO_{2/2}$;

T is $R^3SiO_{3/2}$;

and Q is $SiO_{4/2}$ $R^1$, $R^2$ and $R^3$ are each independently a monovalent hydrocarbon radical; and x and y are each integers, wherein $0 \leq x \leq 10$ and $0 \leq y \leq 10$ and $0 \leq z \leq 10$.

8. The method of claim 7, wherein the linear or branched, volatile siloxane of the present invention comprises octamethyltrisiloxane, decamethyltetrasiloxane, or dodecamethylpentasiloxane or methyltris(trimethylsiloxy)silane.

9. The method of claim 1, wherein the silicone is a cyclic siloxane comprising one or more compounds of the structural formula:

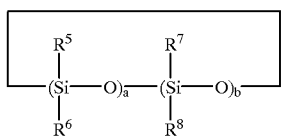

(II)

wherein:

$R^5$, $R^6$, $R^7$ and $R^8$ are each independently a monovalent hydrocarbon group; and a and b are each integers wherein $0 \leq a \leq 10$ and $0 \leq b \leq 10$, provided that $3 \leq (a+b) \leq 10$.

10. The method of claim 9, wherein the cyclic siloxane is octamethylcyclotetrasiloxane or decamethylcyclopentasiloxane.

11. The method of claim 1, wherein the impurities removed are potassium silanolate, potassium hydroxide, tetramethylammonium hydroxide, or a combination thereof.

12. A dry cleaning process comprising:

(a) contacting an article with a silicone solvent;

(b) removing the silicone solvent;

(c) contacting the removed silicone solvent or a weak acid with an aqueous solution that contains an undesirable basic impurity capable of causing cyclic siloxane formation wherein the aqueous solution used is a salt or a weak acid solution; and (d) separating the silicone solvent from the aqueous solution wherein said solvent is purified of said undesirable basic impurity.

13. The process of claim 12, further comprising agitating to ensure good mixing of the silicone solvent and the aqueous solution.

14. The process of claim 12, wherein the aqueous solution used is a solution of sodium chloride, potassium chloride, sodium bromide, magnesium sulfate, acetic acid, citric acid, sorbic acid, sodium carbonate and sodium bicarbonate.

15. The process of claim 12, further comprising drying the silicone solvent with an adsorbent before separating the silicone solvent from the aqueous solution.

16. The process of claim 12, further comprising reusing the treated silicone solvent in step (a).

17. The process of claim 12, wherein the dry cleaning process comprises a plurality of dry cleaning cycles comprising steps (a) and (b), and a plurality of stabilizing cycles comprising steps (c) and (d), wherein the dry cleaning cycle is repeated one or more times per each stabilizing cycle.

18. The method of claim 5 wherein the contact time with the adsorbent is from about 0.001 to about 6 hours.

* * * * *